United States Patent [19]  
Scott et al.

[11] 4,107,818  
[45] Aug. 22, 1978

[54] ANIMAL EUTHANASIA

[75] Inventors: Walter Norris Scott, Letchworth; Judy Anne MacArthur, Salisbury, both of England

[73] Assignee: Universities Federation for Animal Welfare, England

[21] Appl. No.: 748,335

[22] Filed: Dec. 7, 1976

[30] Foreign Application Priority Data

Dec. 11, 1975 [GB] United Kingdom ............... 50765/75

[51] Int. Cl.² ........................................... A61M 16/00
[52] U.S. Cl. ...................................... 17/51; 128/172; 128/204
[58] Field of Search ................. 17/1 R, 1 A, 1 E, 51; 128/203, 204, 1 B, 172, 297, 298, 303 R

[56] References Cited

U.S. PATENT DOCUMENTS

| 1,849,194 | 3/1932 | McCurrie | 128/172 |
| 1,974,843 | 9/1934 | Blashfield | 128/204 X |
| 2,064,822 | 12/1936 | Cramer et al. | 128/172 |
| 2,172,768 | 9/1939 | Liston | 128/303 R |
| 2,244,082 | 6/1941 | Reyniers | 128/1 B |
| 2,737,683 | 3/1956 | Regensburger | 17/1 R |
| 3,356,087 | 12/1967 | Guttman | 128/172 |
| 3,368,556 | 2/1968 | Jensen et al. | 128/204 |
| 3,828,396 | 8/1974 | Wernberg | 17/1 A |

Primary Examiner—Russell R. Kinsey  
Assistant Examiner—Paul J. Hirsch  
Attorney, Agent, or Firm—Seidel, Gonda & Goldhammer

[57] ABSTRACT

A method of euthanasia for small animals, particularly cats, involving inducing hypoxia using a mixture of carbon dioxide and oxygen prior to gassing with carbon dioxide. The initial mixture contains not less than 40% carbon dioxide and not more than 50% oxygen. The apparatus consists of a lidless double chamber with valved gas supplies to the separate chambers.

10 Claims, 3 Drawing Figures

ANIMAL EUTHANASIA

This invention relates to methods of and apparatus for the euthanasia of small animals, in particular cats. The invention is concerned with gaseous euthanasia using carbon dioxide.

It is among the objects of the present invention to provide apparatus for and a method of gaseous euthanasia which is painless and does not induce fear or apprehension in the animal; which is reliable; which is rapid; which is safe and simple to operate; which is inexpensive, and which is, in summary, humane.

It is already known to use gaseous euthanasia for animals using either nitrous oxide, or carbon dioxide, or chloroform vapour. Of these gases, chloroform has a number of disadvantages in that the vapour is irritant and causes excitement during the induction phase, and in addition, if the technique is properly carried out, it is somewhat prolonged. This is particularly so in the case of animals the size of adult cats. Carbon dioxide when used in very high concentrations with the exclusion of substantially all oxygen is not acceptable in that the animals will show symptoms of stress and often exhibit severe convulsive spasms and seizures. Nitrous oxide, although effective in inducing hypoxia, has been found to have certain disadvantages, particularly when compared with carbon dioxide.

The present invention is based upon the use of carbon dioxide to induce hypoxia. Hypoxia is a deficiency in the oxygen available to the body tissues and it is an object of the invention to ensure that the hypoxic state develops insidiously so that the animal will go through the stages of unconsciousness, anaesthesia and death without discomfort or pain. Inhalation of high concentrations of carbon dioxide gas, i.e. concentrations of about 40% or greater, depresses pain sensation in a very short time, generally of the order of ten seconds, by direct action on the central nervous system. Rapid anaesthesia is induced and this becomes lethal if the exposure is prolonged. One of the physiological effects of the inhalation of carbon dioxide is to stimulate respiration, thus helping to ensure a rapid induction of anaesthesia with a minimum period of distress. The concurrent depression of pain sensation is an additional advantage.

In accordance with one aspect of the present invention there is provided a method for the euthanasia of small animals, particularly cats, which comprises filling a first chamber with a gaseous mixture containing not less than 40% carbon dioxide and not more than 50% oxygen, filling a second chamber substantially wholly with carbon dioxide, placing the animal in the first chamber until fully anaesthetised, and then transferring the animal to the second chamber until life is extinct.

Preferably the gaseous mixture in the first chamber comprises at least 60% carbon dioxide and about 30% oxygen.

This method using a not insubstantial concentration of oxygen in the first chamber enables one to achieve anaesthesia without discomfort to the animal, whereas thereafter one can proceed to complete euthanasia at maximum speed by using a maximum concentration of carbon dioxide.

It is important that the concentration of gas in the respective chambers is boosted in between the euthanasia of successive animals in order to maintain the correct concentrations of gas in the two chambers. Preferably, the gases which are passed into the first chamber are passed through water to provide a sufficient degree of humidity, again to minimise discomfort to the animal.

In accordance with another aspect of the invention there is provided apparatus for the euthanasia of small animals, particularly cats, which comprises a first chamber, a second chamber, pipe means leading to each chamber and arranged to be capable of distributing gas uniformly throughout the respective chambers, valve means to control the flow of gases to the respective chambers, and flow rate indicating means connected into said pipe means, the arrangement being such that a mixture of carbon dioxide and oxygen is arranged to be fed to the first chamber through said flow rate indicator means and carbon dioxide alone is arranged to be fed to the second chamber.

Preferably, the two chambers are positioned side-by-side in the form of a lidless box whereby a cage carrying an animal can be lifted readily from the first chamber to the second chamber. Preferably, there is additionally provided means for passing the gases for the first chamber through a water container to humidify the gas mixture.

In order that the invention may be fully understood, reference is now made to the following description and to the accompanying drawings, in which.

Figure 1:
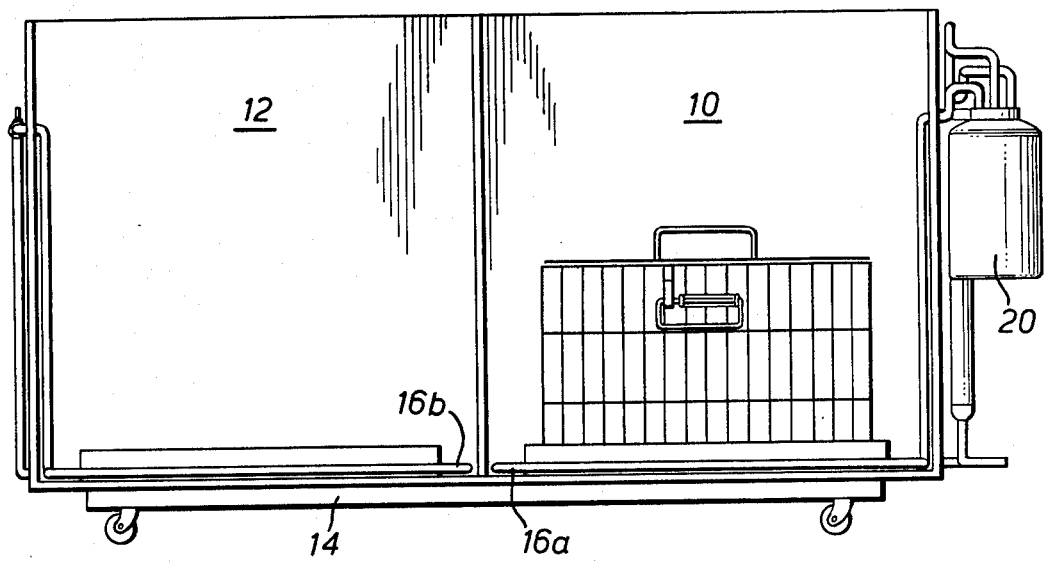
FIG. 1 is a front view of the apparatus of the present invention.
Figure 2:
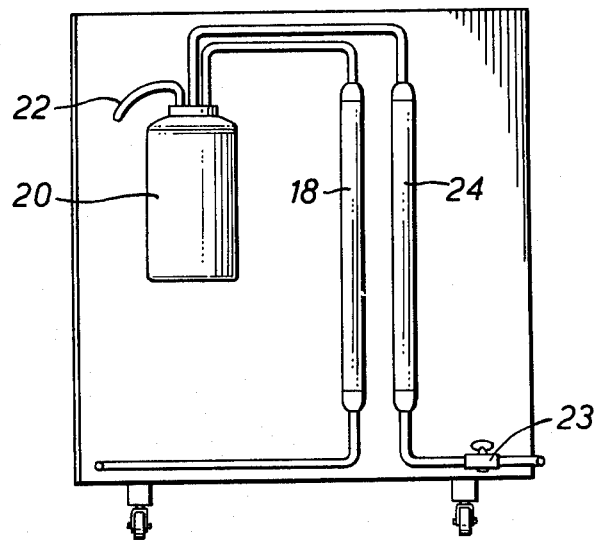
FIG. 2 is an end view of the apparatus as viewed from the right-hand side of FIG. 1; and, FIG. 3 is a top plan view of the apparatus of FIGS. 1 and 2.
Figure 3:
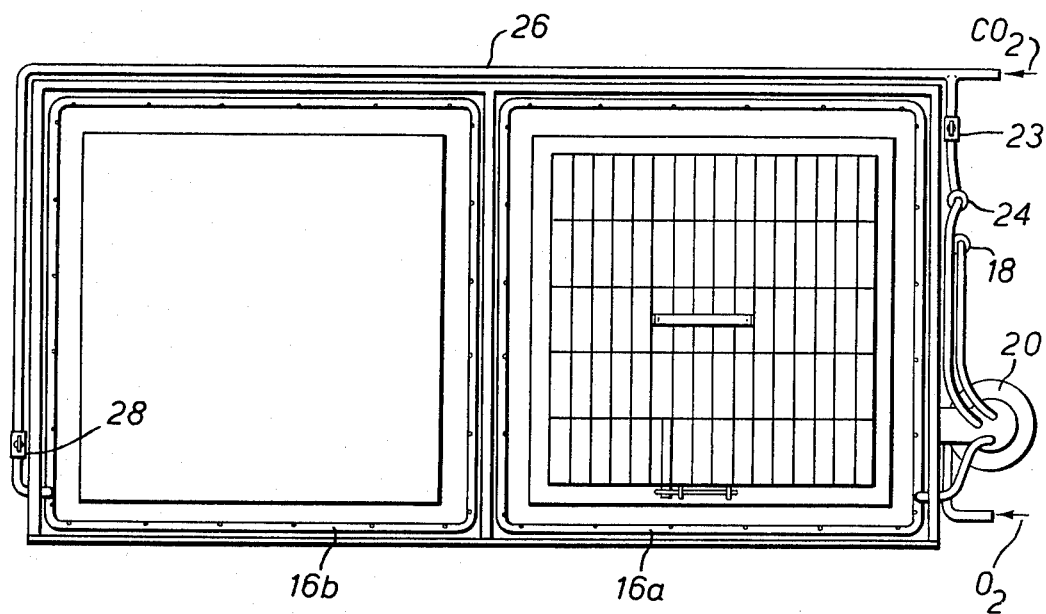

As shown in the drawings the apparatus comprises a first chamber 10 and a second chamber 12 positioned side-by-side on a movable base 14. The front panel of each chamber is made of a transparent material, for example a rigid plastics sheet, and each chamber is left open at the top. Inside each chamber a perforated pipe 16a, 16b extends around the four walls of the chamber and rests upon the base of the chamber. 12mm diameter copper pipe drilled with 3.5 mm diameter holes at 60 mm intervals may be used for example. This disposition of the pipes is designed to produce a uniform distribution of gas within each chamber without excessive turbulence, the filling of each chamber with the gas causing the air in the chamber to be displaced upwardly from the chamber.

Oxygen from a pressure cylinder (not shown) is fed through primary and secondary regulators (not shown) to give precise pressure control of the gas, and is then passed through a flow meter 18. From the flow meter 18 the oxygen passes into oxygen: 20 partially filled with water. The gas which bubbles through the water passes by way of a further pipe 22 into the chamber 10 to join with the distribution pipe 16a. Carbon dioxide gas from a second pressure cylinder (not shown) is similarly fed through primary and seconday regulators (not shown) and can pass through a valve 23 to a flow meter 24. From the flow meter 24 the carbon dioxide passes through the water container 20 and thence to the first chamber 10. Carbon dioxide for the second chamber 12 is taken from the same source but is passed through a pipe 26 and a further valve 28 to join the distribution pipe 16b within the chamber 12.

In order that the chamber 10 shall induce rapid anaesthesia of the animal it is preferable that the gas mixture within the chamber should be substantially in the ratio of 30% oxygen : 70% carbon dioxide. However, if speed of operation is not an important factor then a lesser concentration of carbon dioxide and a greater concentration of oxygen can be used. The gaseous mixture should nevertheless contain not less than 40% carbon dioxide and not more than 50% oxygen, in order to induce hypoxia satisfactorily. The chamber 12 should preferably contain greater than 95% carbon dioxide. It has been found that with the pipe sizes referred to above, and with a flow rate into chamber 10 of about 50 liters per minute of carbon dioxide and 25 liters per minute of oxygen, and with a flow rate into chamber 12 of about 50 liters per minute of carbon dioxide, after allowing the gases to flow for three minutes the desired gas concentrations are obtained in both chambers 10 and 12. The even spacing of the holes in the pipes 16a, 16b helps to reduce turbulence at these flow rates.

The method of euthanasia is as follows. Warm waer at about 100° F is placed in the container 20 in order to provide the humidifying effect on the $CO_2/O_2$ gas mixture. Valve 28 is closed and valve 23 is opened and the carbon dioxide regulator is adjusted until the float in the flow meter 24 reaches the correct precalibrated level. The oxygen regulator is then adjusted until the float in the oxygen flow meter 18 is also at its correct precalibrated level. The mixture of gases is passed into the chamber 10 for example three minutes. The oxygen regulator is then closed, valve 28 is opened and valve 23 is closed. Carbon dioxide is then passed into chamber 12, again for three minutes. The carbon dioxide regulator is then also closed. One can at this stage confirm that the chambers 10, 12 are filled with the gases by testing with a lighted splint. A lighted splint lowered into chamber 10 should continue burning, due to the proportion of oxygen present, whereas a lighted splint lowered into chamber 12 will be extinguished as it is lowered into the upper part of the chamber.

A cage containing the animal, for example a cat, is then placed into chamber 10 for three minutes, by which time the cat will be fully anaesthetised. The cage is then removed from chamber 10 and placed in chamber 12 for a further three minutes, by which time the cat should be dead. At the same time that the animal is in chamber 12 the gas mixture in the first chamber 10 is boosted by passing the correct $CO_2/O_2$ gas mixture into the chamber for a further one minute. The concentration of carbon dioxide in chamber 12 should similarly be boosted either while the cage is in the chamber or alternatively after it has been removed. This boosting of the gases is necessary in view of the disturbance of the gas which necessarily takes place when the cage is lowered into and removed from the respective chambers.

The following table indicates some typical results obtained with cats. Unconsciousness is used to describe the cat when it has collapsed and is relaxed. Anaesthesia refers to an animal in deep surgical anaesthesia when palpebral and pedal withdrawal reflexes are abolished. Death is assumed when no cardiac activity is palpable in the thoracic area.

| Time (minutes) to reach | Identity of cat | % $O_2$ | % $CO_2$ |
|---|---|---|---|
| a) Unconsciousness | | | |
| 1.5 | A | 31.1 | 56.9 |
| 0.75 | B | 33.7 | 63.1 |
| 1.0 | C | 31.8 | 61.5 |
| b) Anaesthesia | | | |
| 3.5 | A | 32.7 | 61.1 |
| 1.75 | B | 33.3 | 62.1 |
| 2.5 | C | 31.8 | 61.5 |

Cat A was placed into chamber 10 before any gas mixture was added, while cat B was killed according to the method routine described above. It will be appreciated that unconsciousness and anaesthesia are achieved more rapidly by prior filling of the chambers with the carbon dioxide/oxygen mixture. Cat C was a three-week old kitten. Each of the cats A, B, C was kept in chamber 10 for six minutes before being moved to the lethal mixture in chamber 12. However, once the animal is anaesthetised, there is no need for further delay and in nearly all cases anaesthesia is achieved in well under three minutes.

Although particular reference has been made above to the euthanasia of cats, the same technique using the same apparatus can be used for the euthanasia of a variety of other small animals, including puppies, mice, rats, gerbils, guinea-pigs and hamsters. In general, the smaller the animal the more rapidly it becomes anaesthetised.

We claim:

1. A method for the euthanasia of small animals which comprises filling a first chamber with a regulated mixture of gases in predetermined proportions containing not less than 40% carbon dioxide and sufficient oxygen to prevent the animal from having convulsions but not more than 50% oxygen, filling a second chamber in a regulated manner substantially wholly with carbon dioxide, after establishment of the correct gas mixture placing the animal in the first chamber and leaving it in said chamber until fully anaesthetised, and then transferring the animal to the second chamber until life is extinct.

2. A method as claimed in claim 1, in which the gaseous mixture in the first chamber comprises at least 60% carbon dioxide and about 30% oxygen.

3. A method as claimed in claim 1, in which the concentration of the gas mixture in the first chamber and of the carbon dioxide in the second chamber is boosted in between the euthanasia of successive animals.

4. A method as claimed in claim 1, in which the proportion of carbon dioxide in the first chamber is substantially 70%.

5. A method as claimed in claim 1, in which the gases are humidified before being passed into the first chamber.

6. Apparatus for the euthanasia of small animals which comprises a first chamber, a second chamber, pipe means leading to each chamber and arranged to be capable of distributing gas uniformly throughout the respective chambers, oxygen supply means and carbon dioxide supply means connected to said pipe means, flow rate indicating means connected to said pipe means, and valve means connected to said pipe means to enable oxygen and carbon dioxide to be supplied to said first chamber in predetermined proportions through said pipe means and said indicating means and to enable carbon dioxide alone to be supplied to said second chamber through said pipe means and said indicating means, the chambers being so constructed that air is displaced therefrom by the admission of gas thereto.

7. Apparatus as claimed in claim 6, in which the two chambers are positioned side-by-side in the form of a lidless box.

8. Apparatus as claimed in claim 6, which includes a water container connected into said pipe means to the first chamber to humidify the gas mixture.

9. Apparatus as claimed in claim 6, which includes a gas distribution pipe extending around the periphery of each chamber at the bottom of the chamber, each said pipe being perforated at intervals along its length.

10. Apparatus as claimed in claim 6, in which at least one wall of each chamber is of transparent plastics material.

* * * * *